(12) United States Patent
Robinson et al.

(10) Patent No.: US 7,589,828 B2
(45) Date of Patent: Sep. 15, 2009

(54) SYSTEM FOR ANALYTE DETERMINATION THAT INCLUDES A PERMUTATIVE GREY SCALE CALIBRATION PATTERN

(75) Inventors: Grenville Arthur Robinson, Rosemarkie (GB); John McInulty, Westhill (GB); Damian Edward Haydon Baskeyfield, Auldeam (GB); Thomas J. O'Reilly, Inverness (GB); Anthony J. Cronshaw, Cambridge (GB)

(73) Assignee: Lifescan Scotland Limited, Inverness (GB)

( * ) Notice: Subject to any disclaimer, the term of this patent is extended or adjusted under 35 U.S.C. 154(b) by 659 days.

(21) Appl. No.: 11/441,572

(22) Filed: May 26, 2006

(65) Prior Publication Data

US 2007/0273902 A1 Nov. 29, 2007

(51) Int. Cl.
*G01N 33/48* (2006.01)
(52) U.S. Cl. .................................... 356/42; 356/243.4
(58) Field of Classification Search .................. 356/42, 356/243.4, 244; 422/55, 56, 57
See application file for complete search history.

(56) References Cited

U.S. PATENT DOCUMENTS

| | | | | |
|---|---|---|---|---|
| 4,523,852 A | * | 6/1985 | Bauer | ........................ 356/421 |
| 4,797,256 A | * | 1/1989 | Watlington, IV | ............. 422/58 |
| 4,867,946 A | * | 9/1989 | Gross et al. | .............. 422/82.09 |
| 5,708,247 A | | 1/1998 | McAleer et al. | |
| 5,989,917 A | | 11/1999 | McAleer et al. | |
| 6,045,567 A | | 4/2000 | Taylor et al. | |
| 6,168,957 B1 | | 1/2001 | Matzinger et al. | |
| 6,706,159 B2 | | 3/2004 | Moerman et al. | |
| 6,733,655 B1 | | 5/2004 | Davies et al. | |
| 7,474,390 B2 | * | 1/2009 | Robinson et al. | ............... 356/42 |
| 7,474,391 B2 | * | 1/2009 | Baskeyfield et al. | ........... 356/42 |
| 2003/0207441 A1 | | 11/2003 | Eyster et al. | |
| 2003/0223906 A1 | | 12/2003 | McAllister et al. | |
| 2004/0015102 A1 | | 1/2004 | Cummings et al. | |
| 2004/0191415 A1 | | 9/2004 | Brewer | |
| 2008/0076184 A1 | * | 3/2008 | Putnam et al. | ............... 436/106 |

FOREIGN PATENT DOCUMENTS

EP 0837320 A2 4/1998

* cited by examiner

*Primary Examiner*—Roy Punnoose (57) ABSTRACT

A system for measuring an analyte in a body fluid sample includes a meter, with a grey scale photodetector module, and a memory module. The system also includes a test strip. The test strip has a substrate with a working surface for receiving the body fluid sample and a reverse surface that is in opposition to the working surface. The test strip also includes a permutative grey scale calibration pattern disposed on either of the working and reverse surfaces, with the permutative grey scale calibration pattern including more than one grey scale region. Moreover, the scale regions of the test strip define a grey scale permutation that uniquely corresponds to a calibration code of the test strip. The grey scale photodetector module is configured to detect the permutative grey scale calibration pattern of the test strip when the test strip is inserted into the meter. The memory module has stored therein a grey scale permutation matrix with a plurality of calibration codes, each of the calibration codes uniquely corresponding to a grey scale permutation of the permutative grey scale calibration pattern.

13 Claims, 5 Drawing Sheets

FIG. 10 ated with two grey scale regions, each with seven dis-
SYSTEM FOR ANALYTE DETERMINATION THAT INCLUDES A PERMUTATIVE GREY SCALE CALIBRATION PATTERN

BACKGROUND OF THE INVENTION

1. Field of the Invention

The present invention relates, in general, to medical devices and, in particular, to methods, systems, test strips, and calibration strips used for the determination of analytes.

2. Description of the Related Art

A variety of systems for determining an analyte (e.g., glucose) in a body fluid sample (for example, a whole blood, plasma or interstitial fluid sample) are known and documented. These systems typically include a meter, at least one test strip, either electrochemical or photometric in nature, and at least one lancet. The lancet can, if desired, be integrated with the test strip. An example of such a system is the One-Touch® Ultra from Lifescan Inc., Milpitas, USA. Further representative systems, meters and test strips are described in, for example, U.S. Pat. Nos. 6,168,957B1; 5,708,247; 6,045,567 and 6,733,655, and US Patent Application Publication Nos. 2004/015102A and 2003/0207441A1, each of which is hereby incorporated in full by reference.

As the manufacturing of conventional test strips is subject to variation, a calibration code (also referred to as a test strip calibration code) is typically assigned to each lot of test strips during the manufacturing process. The calibration code, following entry into an associated meter, is used with an algorithm in the meter to compensate for test strip manufacturing variability. In this manner, an analyte can be determined accurately and precisely regardless of test strip manufacturing variation.

The calibration code assigned to the test strips within any given test strip package (e.g., vial or cassette) purchased by a user can vary from package to package. Therefore, during use of a meter and test strip, a user must ensure that the calibration code that corresponds to the test strip undergoing use has been entered into the meter. This may require that the user obtain a calibration code printed on the test strip package and manually enter that calibration code into the meter or select that calibration code from a list of calibration codes stored in the meter.

Failure to enter or select the calibration code that corresponds to a test strip undergoing use (i.e., the "correct" calibration code) can lead to inaccurate and/or imprecise determination of an analyte. Moreover, the manual entering or selecting of calibration codes is time consuming and can be inconvenient to a user.

BRIEF DESCRIPTION OF THE DRAWINGS

A better understanding of the features and advantages of the present invention will be obtained by reference to the following detailed description that sets forth illustrative embodiments in which the principles of the invention are utilized and the accompanying drawings, of which.

DETAILED DESCRIPTION OF EXEMPLARY EMBODIMENTS THE INVENTION

Figure 1A:
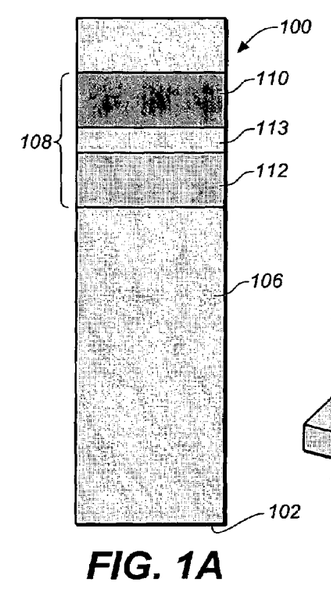
FIGS. 1A and 1B are simplified bottom and perspective views respectively of a test strip according to an exemplary embodiment of the present invention.
Figure 1B:
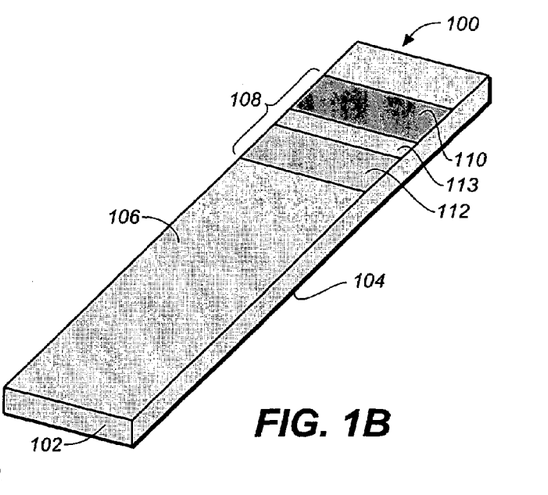

FIGS. 1A and 1B are simplified bottom and perspective views respectively of a test strip 100 for the determination of an analyte (such as glucose) in a body fluid sample (e.g. a whole blood sample) according to an exemplary embodiment of the present invention. Test strip 100 includes a substrate 102 with a working surface 104 (not visible in the perspective of FIGS. 1A and 1B) for receiving the body fluid sample and a reverse surface 106 in opposition to working surface 104.

Test strip 100 also includes a permutative grey scale calibration pattern 108 disposed on reverse surface 106. In the embodiment of FIGS. 1A and 1B, the permutative grey scale calibration pattern 108 includes a first grey scale region 110 and a second grey scale region 112, with the first and second grey scale regions 110 and 112, respectively, being spaced apart by gap 113. However, once apprised of the present disclosure, one skilled in the art will recognize that grey scale calibration patterns employed in embodiments of the present invention can include a plurality of grey scale regions that are not spaced apart by a gap. In this respect, gap 113 can be considered optional. As is explained in further detail below, the combination of first grey scale region 110 and second grey scale region 112 define a grey scale permutation that uniquely corresponds to a calibration code that has been assigned to test strip 100. The term "grey scale," as employed herein, refers to an optical characteristic of a surface measured via reflection at a single wavelength with the intensity of reflection (i.e., reflection intensity) corresponding to a grey scale level.

Substrate 102 can be formed from any suitable substrate material known to one skilled in the art including, but not limited to, polymeric substrates (such as the commercially polymeric substrate materials Melinex® ST348, manufactured by DuPont, Teijin Films), paper substrates and fibrous substrates. The substrate surface upon which the permutative grey scale calibration pattern is disposed can have a finish (e.g., a matte finish or a gloss finish) that facilitates efficient detection of the permutative grey scale pattern by a predetermined means (e.g., static optical detection).

Once apprised of the present disclosure one skilled in the art will recognize that working surface 104 refers to the surface of a test strip that includes, for example, electrodes and/or analytical reagents of either a photometric or electrochemical nature.

In the embodiment of FIGS. 1A and 1B first and second grey scale regions 110 and 112, respectively, are disposed directly on reverse surface 106. This can be accomplished, for example, by any suitable conventional grey scale printing technique such as dithered printing, ink-jet printing, screen-printing, pad printing, lithographic printing, flexographic printing and combinations thereof. Such printing techniques can employ, for example, any suitable ink including, for example, ultra-violet cured inks, non-aqueous solvent-based inks and aqueous inks. Non-limiting examples of inks that may be suitable (depending on substrate, printing technique and detection technique) include Festival Intense Process Black ink (Product Ref. Code: Fest-24) commercially available from Coates, UK and Supra UV Offset Black Ink (Product No. 567503) commercially available from Jänecke & Schneeman Druckfarben, Hanover, Germany. Predetermined grey scale levels can be created using conventional grey scale printing techniques by, for example, printing predetermined black ink dot densities on a substantially white background.

Grey scale regions employed in embodiments of the present invention can also be formed using suitable laser ablation and reactive pigment marking techniques known to those of skill in the art. Alternatively, the grey scale regions can be formed on an adhesive tape or label with the tape or label being subsequently affixed to the substrate of a test strip. Moreover, the permutative grey scale calibration pattern can have a finish (e.g., a varnished finish, an unvarnished finish, a gloss finish, a satin finish or a matte finish) that facilitates efficient detection of the permutative grey scale pattern by a predetermined means (e.g., static optical detection). Any suitable varnish known to one skilled in the art can be employed to create a varnished finish. Examples of varnishes that may be suitable include, but are not limited to, Pulse EL215 Matt Flexo Lacquer (commercially available from Pulse Roll Label Products, Bristol, UK) and Senolith UV Inline Varnish Reference 360022 (commercially available from Wellberger Graphics Gmbh, Germany).

Although, for the purpose of illustration only, a permutative grey scale calibration pattern is depicted as being disposed on the reverse surface, it can be disposed on either of the working and reverse surfaces. Since a user's attention is typically focused on the working surface of a test strip, disposing a permutative grey scale calibration pattern on the reverse surface can beneficially avoid distracting and/or causing undue concern to a user. However, should a user's attention be drawn to the permutative grey scale calibration pattern, such patterns are believed to be aesthetically pleasing and, therefore, unlikely to distract or disturb a user.

Test strips that include a permutative grey scale calibration pattern with a plurality of grey scale regions are advantageous in comparison to a test strip that includes a conventional bar code since the optical registration tolerance required to successfully detect grey scale regions can be less restrictive than the optical tolerance required to successfully detect a conventional bar code. The less restrictive tolerances enable the use of robust, simple and inexpensive printing and registration techniques for the formation of the grey scale regions and simplify meter construction.

Figure 2:
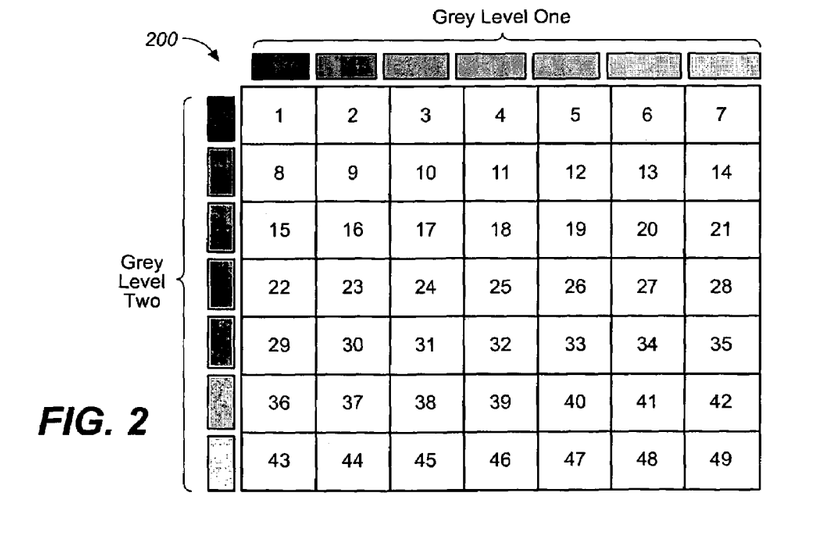
FIG. 2 depicts a matrix of forty nine unique permutations associated with two grey scale regions, each with seven distinct grey scale levels.

FIG. 2 depicts a matrix 200 of forty-nine grey scale permutations (i.e. a seven-by-seven matrix) associated with two grey scale regions (labeled grey level one and grey level two in FIG. 2) for the circumstance where each grey scale region is one of seven distinct predetermined grey scale levels. One skilled in the art will recognize that the two grey scale regions (i.e. corresponding to grey level one and grey level two of FIG. 2) can be, for example, first grey scale region 110 and second grey scale region 112 of test strip 100 described above or any two grey scale regions included in embodiments of the present invention.

Once the grey scale level of each of the two grey scale regions has been detected (for example, by an optical sensor incorporated into a meter), the two grey scale levels define a grey scale permutation that uniquely corresponds to one of forty nine calibration codes (depicted by the numbers 1 through 49 in FIG. 2). For example, if grey level one is detected as the mid-point level of the seven distinct predetermined grey scale levels and grey level two is detected as the lightest of the seven distinct predetermined grey scale levels, then the uniquely corresponding calibration code is code forty-six (46). Therefore, by employing tests strips with a permutative grey scale calibration pattern as described herein the calibration code that has been assigned to the test strip can be automatically and uniquely determined by a meter without any user intervention.

If desired, each grey scale permutation can also correspond to additional data, other than a calibration code, associated with a lot of test strips. For example, each grey scale permutation can also correspond to a test strip lot expiration date or test strip product identification.

Although, for the purpose of explanation only, a seven-by-seven matrix based on seven distinct predetermined grey scale levels is depicted in FIG. 2, one skilled in the art will recognize that such a matrix can be based on any suitable number of distinct predetermined grey scale levels. For example, a 10-by-10 matrix based on ten grey distinct predetermined grey scale levels for both grey level one and grey level two can contain one hundred unique calibration codes. The number and choice of distinct predetermined grey scale levels can be based on, for example, the ability of an associated optical sensor to accurately and reliably detect and distinguish between the distinct predetermined grey scale levels and the ability to accurately and reliably manufacture the distinct predetermined grey scale levels.

Figures 3A, 3B:
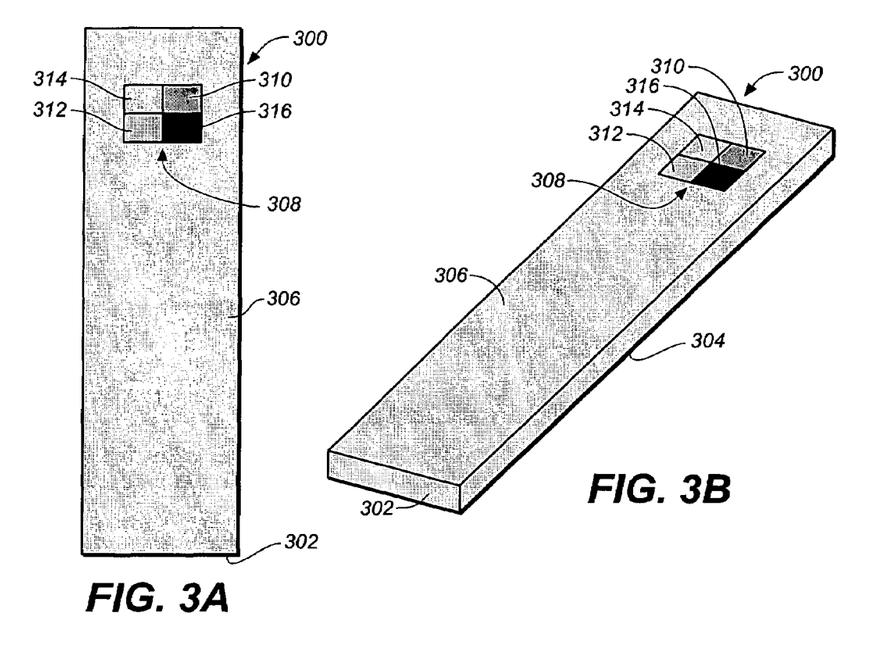
FIGS. 3A and 3B are simplified bottom and perspective views respectively of a test strip according to another exemplary embodiment of the present invention.

FIGS. 3A and 3B are simplified bottom and perspective views respectively of a test strip 300 for the determination of an analyte in a body fluid sample according to another exemplary embodiment of the present invention. Test strip 300 includes a substrate 302 with a working surface 304 (not visible in the perspective views of FIGS. 3A and 3B) for receiving the body fluid sample and a reverse surface 306 in opposition to working surface 304.

Test strip 300 also includes a permutative grey scale calibration pattern 308 disposed on reverse surface 306. In the embodiment of FIGS. 3A and 3B, permutative grey scale calibration pattern 308 includes a first grey scale region 310, a second grey scale region 312, a white optics calibration region 314 and a black optics calibration region 316.

As explained previously, the combination of first grey scale region 310 and second grey scale region 312 constitute a grey scale permutation that, via a permutation matrix, uniquely corresponds to a calibration code that has been assigned to test strip 300. Moreover, in the embodiment of FIGS. 3A and 3B, white optics calibration region 314 and black optics calibration region 316 have also been provided to facilitate calibration of the optics used to detect first grey scale region 310 and second grey scale region 312 at the extremes of the grey scale. For example, the measured reflection intensity of white and black optics calibration regions can be compared to expected intensities, with any differences therebetween used as a basis for calibration of the optics. It is postulated, without being bound, that such calibration will improve the optic's accuracy with respect to grey scale detection.

Figure 4:
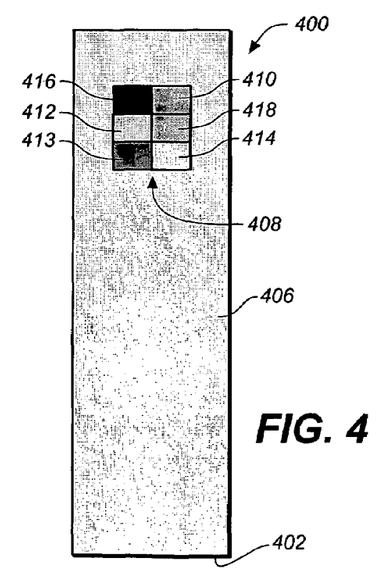
FIG. 4 is a simplified bottom view of a test strip according to still another exemplary embodiment of the present invention.

FIG. 4 is a simplified bottom view of a test strip 400 for the determination of an analyte in a body fluid sample according to still another exemplary embodiment of the present invention. Test strip 400 includes a substrate 402 with a working surface (not visible in the perspective of FIG. 4) for receiving the body fluid sample and a reverse surface 406 in opposition to the working surface.

Test strip 400 also includes a permutative grey scale calibration pattern 408 disposed on reverse surface 406. In the embodiment of FIG. 4 permutative grey scale calibration pattern 408 includes a first grey scale region 410, a second grey scale region 412, a third grey scale region 413, a white optics calibration region 414, a black optics calibration region 416, and a 50% grey scale calibration region 418.

The combination of first grey scale region 410, second grey scale region 412 and third grey scale region 413 constitute a grey scale permutation that uniquely corresponds, via a three-dimensional matrix, to a calibration code that has been assigned to test strip 400. For example, assuming that the first, second and third grey scale regions are each detected at one of seven distinct predetermined grey scale levels, a seven-by-seven-by-seven three-dimensional matrix can be employed to determine which of three hundred and forty three calibration codes uniquely corresponds to a given permutative grey scale calibration pattern.

Moreover, in the embodiment of FIG. 4, white optics calibration region 414, black optics calibration region 416 and 50% grey scale calibration region 418 facilitate calibration of the optics used to detect first grey scale region 410, second grey scale region 412 and third grey scale region 413 at the extremes and the mid-point of the grey scale.

Figure 5:
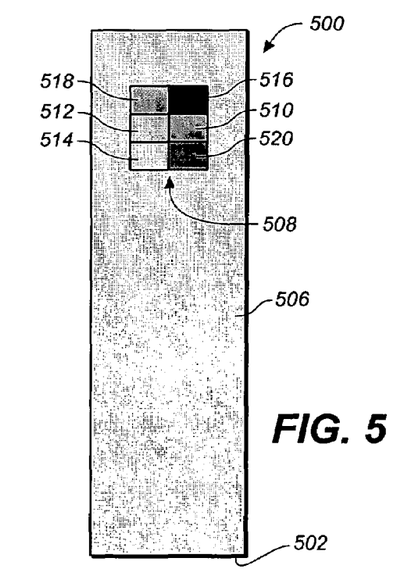
FIG. 5 is a simplified bottom view of a test strip according to yet another exemplary embodiment of the present invention.

FIG. 5 is a simplified bottom view of a test strip 500 for the determination of an analyte in a body fluid sample according to yet another exemplary embodiment of the present invention. Test strip 500 includes a substrate 502 with a working surface (not visible in the perspective of FIG. 5) for receiving the body fluid sample and a reverse surface 506 in opposition to the working surface.

Test strip 500 also includes a permutative grey scale calibration pattern 508 disposed on reverse surface 506. In the embodiment of FIG. 5 permutative grey scale calibration pattern 508 includes a first grey scale region 510, a second grey scale region 512, a white optics calibration region 514, a black optics calibration region 516, a 25% grey scale optics calibration region 518 and a 75% grey scale optics calibration region 520.

As previously described, the combination of first grey scale region 510 and second grey scale region 512 constitutes a grey scale permutation that uniquely corresponds to a calibration code that has been assigned to test strip 500 during manufacturing. For example, after a calibration code specific to a lot (i.e. batch) of test strips being manufactured has been determined via laboratory testing or other suitable method the permutative grey scale calibration pattern that corresponds to that calibration code can be disposed on each of the test strips of the lot using techniques described above with respect to test strip 100.

Moreover, in the embodiment of FIG. 5, white optics calibration region 514, black optics calibration region 516 and 25% grey scale optics calibration region 418 and 75% grey scale optics calibration region 420 facilitate calibration of optics used to detect first grey scale region 510 and second grey scale region 512 at the extremes, 25% and 75% levels of the grey scale.

Although, for the purpose of illustration only, permutative grey scale calibration patterns have been depicted as including grey scale regions shaped as discrete bands (see FIG. 1) and essentially square-shaped adjoining regions (see FIGS. 3A, 3B, 4 and 5) disposed in the center of the substrate's reverse surface (see FIGS. 3A, 3B, 4 and 5), the permutative grey scale calibration patterns of test strips according to the present invention can take any suitable shape and be disposed at any suitable position on either of the working and reverse surfaces of the test strip substrate. The suitability of any given shape and position will be, however, dependent on characteristics of the optics used to detect the grey scale regions. Such characteristics include, for example, the size and shape of the optics detection area and positional tolerances associated with both the optics and the disposition of the permutative grey scale calibration pattern on the substrate.

Figure 6:
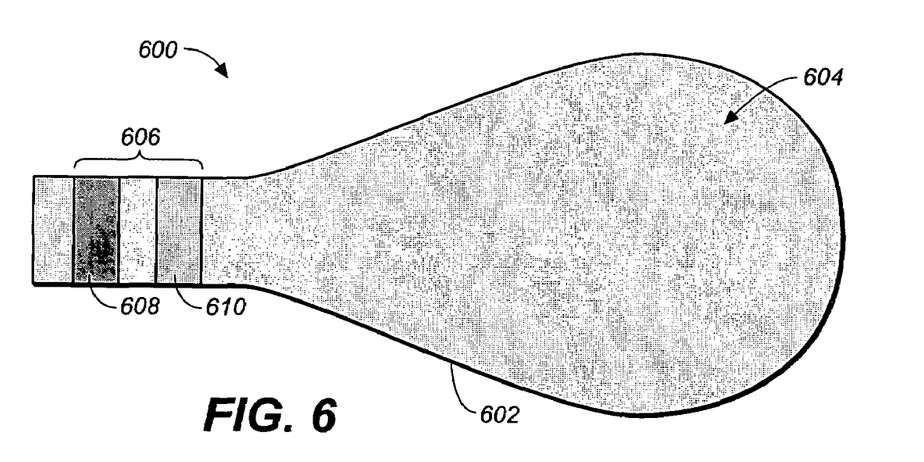
FIG. 6 is a simplified top view of a calibration strip according to an exemplary embodiment of the present invention.

FIG. 6 is a simplified top view of a calibration strip 600 according to an exemplary embodiment of the present invention for use with a package of test strips. It is envisioned that calibration strip 600 would be employed by a user to enter a calibration code into a meter in a circumstance where the test strips themselves do not include a permutative grey scale calibration pattern.

Referring to FIG. 6, calibration strip 600 includes a substrate 602 with a substrate surface 604 and a permutative grey scale calibration pattern 606. Permutative grey scale calibration pattern 606 is disposed on substrate surface 604 and includes a first grey scale calibration region 608 and a second grey scale calibration region 610. Moreover, first and second grey scale calibration regions 608 and 610 define a grey scale permutation that uniquely corresponds to a calibration code of test strips in a package (e.g. a vial or other dispenser) associated with the calibration strip.

Substrate 602 can be formed from any suitable substrate material known to one skilled in the art including, but not limited to, commercially available substrate materials such as Melinex® ST348 manufactured by DuPont, Teijin Films. Suitable substrate materials can be semi-rigid and of the same dimensions and shape as the associated test strips. However, the embodiment of FIG. 6 has a paddle shape that facilitates ease of handling.

Once apprised of the present disclosure, one skilled in the art will recognize that the permutative grey scale calibration pattern employed on calibration strips according to embodiments of the present invention can take any of the characteristics discussed above for permutative grey scale calibration patterns employed on test strips according to embodiments of the present invention. For example, the permutative grey scale calibration pattern employed on a calibration strip can include two or more grey scale regions and, optionally, optics calibration region(s).

Figure 7:
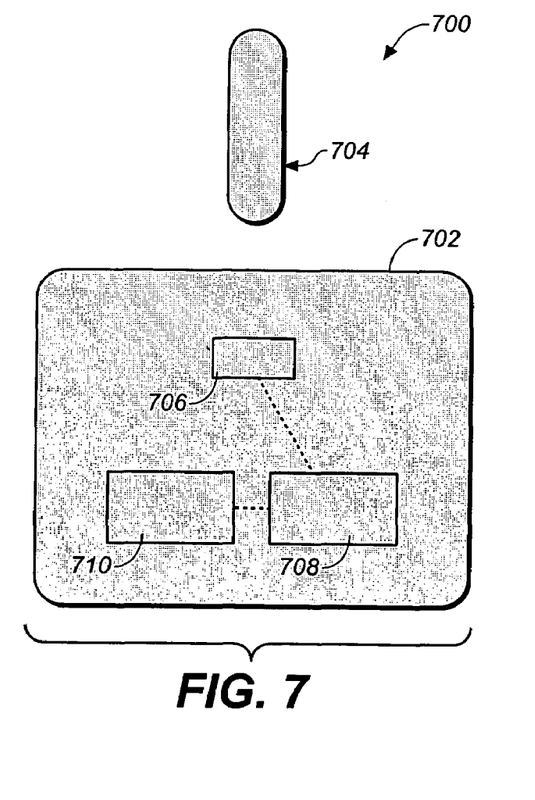
FIG. 7 is a simplified block diagram of a system according to an exemplary embodiment of the present invention.
Figure 8A:
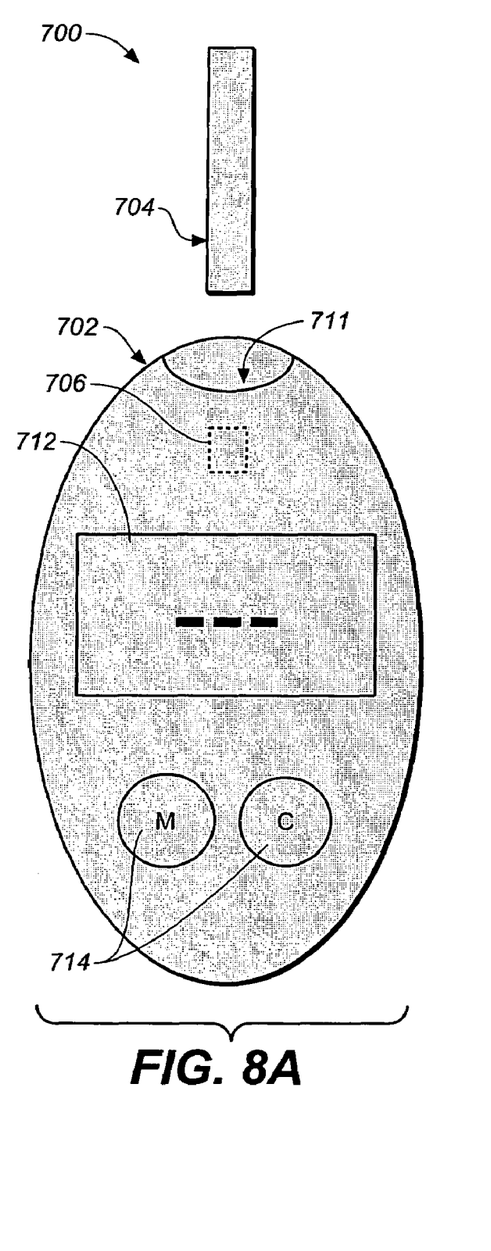
FIGS. 8A and 8B are simplified front and side schematic views, respectively, of a meter and test strip of a system according to an exemplary embodiment of the present invention.
Figure 8B:
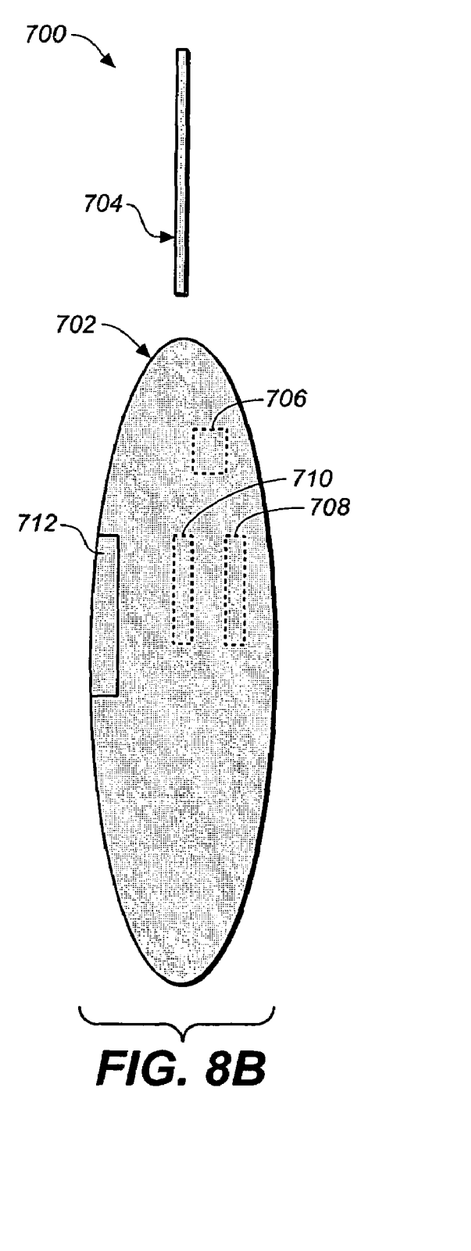

FIG. 7 is a simplified block diagram of a system 700 for determining, for example, the presence of concentration of an analyte according to an exemplary embodiment of the present invention. FIGS. 8A and 8B are simplified front and side schematic views respectively of a meter and test strip of system 700 that serve to further illustrate various features of system 700.

Referring to FIGS. 7, 8A and 8B system 700 includes a meter 702 and at least one test strip 704. Meter 702 includes a grey scale photodetector module 706 (also referred to simply as "optics"), a memory module 708 and a microprocessor module 710. Dashed lines in FIG. 7 indicate communication paths between various components of meter 702.

Although not depicted in FIGS. 7, 8A and 8B test strip 704 includes features according to the test strip embodiments described herein including those of FIGS. 1A, 1B, 3A, 3B, 4 and 5. In other words, test strip 704 is a test strip for the determination of an analyte, such has glucose, in a body fluid sample (for example, a whole blood sample) and includes a substrate with a working surface for receiving the body fluid sample and a reverse surface that is in opposition to the working surface. Test strip 704 also includes a permutative grey scale calibration pattern disposed on either of the working and reverse surfaces with the permutative grey scale calibration pattern including more than one grey scale region. Moreover, the grey scale regions of test strip 704 define a grey scale permutation that uniquely corresponds to a calibration code of the test strip.

Grey scale photodetector module 706 (also referred to as "optics") is configured to detect the permutative grey scale calibration pattern of test strip 704 when the test strip is inserted into meter 702 (for example, insertion via insertion port 711). As previously noted, the term "grey scale" refers to an optical characteristic that is measured via reflection at a single wavelength with the intensity of reflection corresponding to a grey scale level. Therefore, the grey scale photodetector employed in systems according to the present invention is configured to detect the various levels of grey scale within grey scale regions of the permutative grey scale calibration pattern using single wavelength reflective measurement techniques.

Moreover, memory module 708 has stored therein a grey scale permutation matrix with a plurality of calibration codes, each of the calibration codes uniquely corresponding to a grey scale permutation of the permutative grey scale calibration pattern. The grey scale permutation matrix stored within memory module 708 can take any suitable form including, for example, the form of FIG. 2. Microprocessor module 710 is configured to employ a calibration code in an algorithm during the determination of an analyte concentration in a body fluid sample. In the embodiment of FIGS. 7, 8A and 8B, meter 702 also includes a display 712 and user operable buttons 714.

Once apprised of the present disclosure, one skilled in the art will recognize that meters suitable for employment in systems according to embodiments of the present invention can obtained by the modification of conventional meters including, but limited to, conventional meters described in U.S. Pat. Nos. 6,706,159B2 and 5,989,917 and U.S. Patent Application Publication Nos. US2004/0191415A1 and US2003/0223906A1, each of which is hereby incorporated in full by reference. Such modification would entail, for example, the operable incorporation of a grey scale photodetector module and a memory module with a grey scale permutation matrix stored therein.

Figure 9:
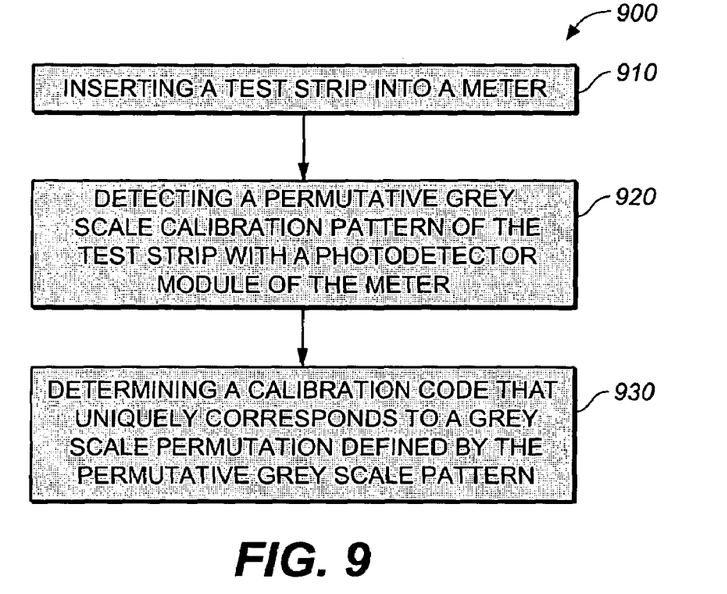
FIG. 9 is a flow diagram of a method according to an exemplary embodiment of the present invention.

FIG. 9 is a flow diagram of a method 900 for determining a test strip calibration code for use in a meter according to an embodiment of the present invention. Method 900 includes inserting a test strip into the meter as set forth in step 910. The inserted test strip has a working surface for receiving the body fluid sample and a reverse surface that is in opposition to the working surface.

The inserted test strip also has a permutative grey scale calibration pattern disposed on at least one of the working surface and reverse surface. Moreover, the permutative grey scale calibration pattern includes at least a first grey scale region and a second grey scale region with the first and second grey scale regions defining a grey scale permutation that uniquely corresponds to a calibration code of the test strip.

Moreover, the test strip employed in methods according to embodiments of the present invention can have any of the characteristics and features described herein with respect to test strips according to embodiments of the present invention.

Method 900 also includes detecting the permutative grey scale calibration pattern with a grey scale photodetector module of the meter (see step 920) and determining a calibration code that uniquely corresponds to a grey scale permutation defined by the permutative grey scale calibration pattern based on permutation matrix stored in the meter (see step 930). The determination of the calibration code can be accomplished using the techniques described above with respect to test strips and systems according to embodiments of the present invention.

If desired to conserve meter power, for example, the grey scale photodectector module employed to detect the permutative grey scale calibration pattern can be powered on only after a test strip has been inserted into the meter and powered off once the step of determining the calibration code is complete. Moreover, once apprised of the present disclosure, one skilled in the art will recognize that the permutative grey scale calibration pattern can be detected while in a "static" mode wherein the test strip is stationary within the meter following insertion or a "dynamic" mode wherein the detection occurs as the test strip is undergoing insertion into the meter or undergoing removal from the meter.

Figure 10:
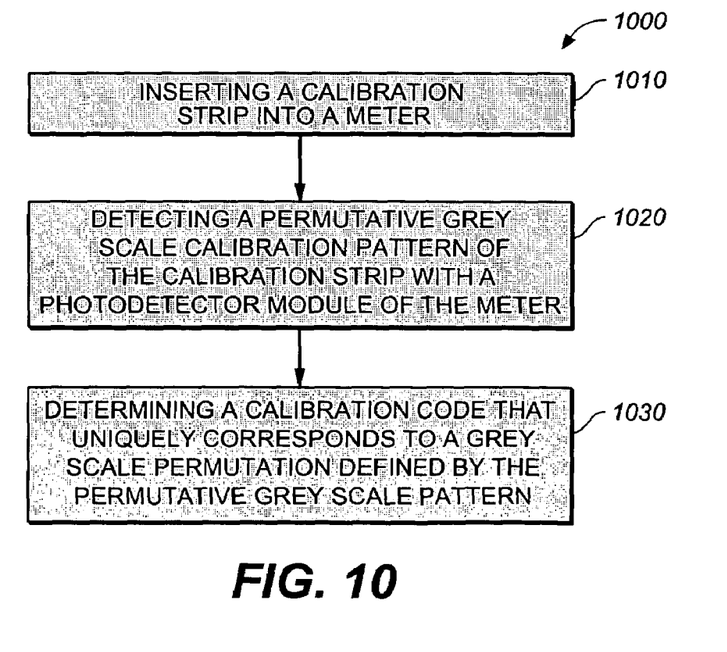
FIG. 10 is a flow diagram of method according to another exemplary embodiment of the present invention.

FIG. 10 is a flow diagram of a method 1000 for determining a test strip calibration code for use in a meter according to an exemplary embodiment of the present invention. Method 1000 includes inserting a calibration strip into the meter as set forth in step 1010.

The calibration strip inserted in step 1010 includes a substrate with a surface and a permutative grey scale calibration pattern disposed on the surface. Moreover, the permutative grey scale calibration pattern includes at least a first grey scale region and a second grey scale region. In addition, the calibration strip employed in methods according to embodiments of the present invention can have any of the characteristics and features described herein with respect to calibration strips according to embodiments of the present invention.

Method 1000 also includes detecting the permutative grey scale calibration pattern with a grey scale photodetector module of the meter (see step 1020) and determining a calibration code that uniquely corresponds to a grey scale permutation defined by the permutative grey scale calibration pattern based on a permutation matrix stored in the meter (see step 1030). The determination of the calibration code can be accomplished using the techniques described above with respect to test strips, calibration strips and systems according to embodiments of the present invention.

If desired to conserve meter power, for example, the grey scale photodectector module employed to detect the permutative grey scale calibration pattern can be powered on only after a calibration strip has been inserted into the meter and powered off once the step of determining the calibration code is complete. Moreover, once apprised of the present disclosure, one skilled in the art will recognize that the permutative grey scale calibration pattern can be detected while in a "static" mode wherein the calibration strip is stationary within the meter following insertion or a "dynamic" mode wherein the detection occurs as the calibration strip is undergoing insertion into the meter or undergoing removal from the meter.

It should be understood that various alternatives to the embodiments of the invention described herein may be employed in practicing the invention. It is intended that the following claims define the scope of the invention and that structures and methods within the scope of these claims and their equivalents be covered thereby.

What is claimed is:

1. A system for measuring an analyte in a body fluid sample, the system comprising;
    a meter with:
        a grey scale photodetector module; and
        a memory module; and
    at least one test strip,
        wherein the test strip includes:
            a substrate, the substrate having:

a working surface for receiving the body fluid sample; and a reverse surface that is in opposition to the working surface; and a permutative grey scale calibration pattern disposed on at least one of the working surface and reverse surface, the permutative grey scale calibration pattern including at least a first grey scale region and a second grey scale region, wherein the grey scale shade of the at least first and second grey scale regions constitute a grey scale permutation that uniquely corresponds to a calibration code, and wherein the grey scale photodetector module is configured to detect the permutative grey scale calibration pattern of the test strip when the test strip is inserted into the meter, and wherein the memory module has stored therein a grey scale permutation matrix with a plurality of calibration codes, each of the calibration codes uniquely corresponding to a grey scale permutation of the permutative grey scale calibration pattern.

2. The system of claim 1 further including a microprocessor module configured to employ a calibration code in an algorithm during the determination of an analyte in a body fluid sample.

3. The system of claim 1 wherein the test strip has the permutative grey scale calibration pattern is disposed on the reverse surface.

4. The system of claim 1 wherein the permutative grey scale calibration pattern includes two grey scale regions.

5. The system of claim 1 wherein the permutative grey scale calibration pattern includes a first grey scale region, a second grey scale region and a third grey scale region.

6. The system of claim 1 wherein the grey scale calibration pattern further includes at least one optics calibration region.

7. The system of claim 6 wherein the at least one optics calibration region has a black optics calibration region and a white optics calibration region.

8. The system of claim 6 wherein the at least one optics calibration region further has a 50% grey scale optics calibration region.

9. The system of claim 6 wherein the at least one optics calibration region further has a 25% grey scale optics calibration region and a 75% grey scale optics calibration region.

10. The system of claim 1 wherein the test strip is an electrochemical test strip.

11. The system of claim 10 wherein the test strip is configured for the determination of glucose in a whole blood sample.

12. The system of claim 1 wherein the test strip is a photometric test strip.

13. The system of claim 12 wherein the test strip is configured for the determination of glucose in a whole blood sample.

* * * * *

UNITED STATES PATENT AND TRADEMARK OFFICE
CERTIFICATE OF CORRECTION

PATENT NO. : 7,589,828 B2  Page 1 of 1
APPLICATION NO. : 11/441572
DATED : September 15, 2009
INVENTOR(S) : Robinson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 771 days.

Signed and Sealed this

Twenty-first Day of September, 2010

David J. Kappos
*Director of the United States Patent and Trademark Office*